US005731326A

United States Patent [19]
Hart et al.

[11] Patent Number: 5,731,326
[45] Date of Patent: Mar. 24, 1998

[54] PDGF ANTAGONISTS II

[75] Inventors: Charles E. Hart, Brier; Mark W. Orme; Kristen M. Moynihan, both of Seattle, all of Wash.

[73] Assignee: ZymoGenetics, Inc., Seattle, Wash.

[21] Appl. No.: 657,470

[22] Filed: May 29, 1996

Related U.S. Application Data

[60] Provisional application No. 60/000,743, Jun. 30, 1995.

[51] Int. Cl.[6] .................. A61K 31/445; A61K 31/40; A61K 31/405
[52] U.S. Cl. .................. 514/323; 514/414; 514/415; 514/418
[58] Field of Search ................ 514/323, 414, 514/415, 418

[56] References Cited

U.S. PATENT DOCUMENTS 5,280,016  1/1994  Conrad et al. ............... 514/56

FOREIGN PATENT DOCUMENTS 568 310 A1  11/1993  European Pat. Off. .
0 604 853 A3  7/1994  European Pat. Off. .

OTHER PUBLICATIONS

Peuler et al., *American Journal of Hypertension* 9: 188–192, 1996.
Ambrogi et al., *Arzneim.-Forsch (Drug Res.)* 21: 204–208, 1971.
Kimura et al., *Japan J. Pharmacol.* 59: 51–56, 1992.
Cavari et al., *Cell Biol. Intl.* 17(8): 781–786, 1993.
Castellot et al., *J. Cell. Biol.* 109(6): 3147–3155, 1989.
Reilly et al., *J. Cell. Phys.* 136: 23–32, 1988.
Guyton et al., *Circulation Research* 46(5): 625–634, 1980.
Popma et al., *Circulation* 84(3); 1426–1436, 1991.
Ferrell et al., *Circulation* 85(4): 1630–1631, 1992.
Lindner et al., *J. Clin. Invest.* 90: 2044–2049, 1992.
Jawien et al., *J. Clin. Invest.* 89: 507–511, 1992.
Lindner et al., *J. Clin. Invest.* 85: 2004–2008, 1990.
Currier et al., *JACC* 17: 118B–125B, 1991.
Schmid et al., *Seminars in Thrombosis and Hemostasis* 19, Suppl. 1: 155–159, 1993.
Edelman et al., *Proc. Natl. Acad. Sci. USA* 87: 3773–3777, 1990.
Rubin et al., *Lancet* Jun. 18, 1988: 1353–1356, 1988.
Buchwald et al., *Circulation* 86(2): 531–537, 1992.

*Primary Examiner*—Kimberly Jordan
*Attorney, Agent, or Firm*—Susan E. Lingenfelter

[57] ABSTRACT

Methods for inhibiting intimal hyperplasia in the vasculature of mammals, including primates, are disclosed. The methods comprise administering to the mammal a non-peptide PDGF antagonist such as 4-(2-(N-(2-carboxamidoindole) aminoethyl)-benzenesulfonamides or sulfonylureas. The methods are useful in reducing intimal hyperplasia due to, for example, vascular injuries resulting from angioplasty, endarterectomy, reduction atherectomy or anastomosis of a vascular graft. The non-peptide PDGF antagonists may optionally be administered coordinately with heparin, whereby the coordinately administered of non-peptide PDGF antagonist and heparin are combinatorially effective in inhibiting intimal hyperplasia.

21 Claims, No Drawings

PDGF ANTAGONISTS II

This application claims the benefit of U.S. Provisional Application No. 60/000,743, filed Jun. 30, 1995.

BACKGROUND OF THE INVENTION

Proliferation of smooth muscle cells (SMCs) in the vessel wall is an important event in the formation of vascular lesions in atherosclerosis, after vascular reconstruction or in response to other vascular injury. For example, treatment of atherosclerosis frequently includes the clearing of blocked vessels by angioplasty, endarterectomy or reduction atherectomy, or by bypass grafting, surgical procedures in which atherosclerotic plaques are compressed or removed through catheterization (angioplasty), stripped away from the arterial wall through an incision (endarterectomy) or bypassed with natural or synthetic grafts. These procedures remove the vascular endothelium, disturb the underlying intimal layer, and result in the death of medial SMCs. This injury is followed by medial SMC proliferation and migration into the intima, accompanied by excessive deposition of extracellular matrix. This lesion development characteristically occurs within the first few weeks and up to six months after injury and stops when the overlying endothelial layer is reestablished. In humans, these lesions are composed of about 20% cells and 80% extracellular matrix.

In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis.

A similar process of SMC proliferation has also been observed in organ transplants, and may contribute to transplant atherosclerosis and organ failure. The intimal thickening in this process involves only the grafted organ.

It has been postulated that platelet mitogens, such as platelet derived growth factor (PDGF), play a role in the development of atherosclerotic plaques (see Ross et al., *Cell* 46: 155–169, 1986; Harker, *Am. J. Cardiol.* 60: 20B–28B, 1987). One proposed mechanism for plaque formation is the release by platelets, at sites of endothelial denudation, of growth factors that stimulate SMC growth (Ross and Glomset, *N. Eng. J. Med.* 295: 369–377, 420–425, 1976; Ross, *Arteriosclerosis* 1: 293–311, 1981). Moore et al. (*Thrombos. Haemostas. (Stuttg.)* 35: 70, 1976) and Friedman et al. (*J. Clin. Invest.* 60: 1191–1201, 1977), using an indwelling catheter injury model, reported an inhibition of experimentally induced intimal lesion formation in rabbit arteries by prolonged thrombocytopenia induced by administration of anti-platelet serum. It has also been postulated that SMCs may themselves produce PDGF which stimulates lesion development through an autocrine mechanism (Ross et al., ibid; Walker et al., *Proc. Natl. Acad. Sci. USA* 83: 7311–7315, 1986). Fingerle et al. (*Proc. Natl. Acad. Sci. USA* 86: 8412–8416, 1989) investigated intimal lesion formation in thrombocytopenic rats and concluded that platelets do not play a role in the initial SMC proliferation after balloon injury but may regulate SMC migration into the intima. Platelets are now known to release a number of growth factors, including PDGF, epidermal growth factor (EGF), transforming growth factors alpha and beta (TGFα and TGFβ), insulin-like growth factor I (IGF-I) and platelet derived endothelial cell growth factor, as well as several chemoattractant molecules. Although certain studies implicate PDGF in processes associated with lesion development, the etiology of intimal hyperplasia in primates, remains undefined.

Removal of atherosclerotic plaques by angioplasty or endarterectomy has limited efficacy, and no effective treatment for restenosis of treated vessels or stenosis of bypass grafts has been developed. There is therefore a need in the art for methods of reducing or preventing the development of SMC-rich lesions in vascular walls, including stenosis of blood vessels following vascular injury, such as injury due to balloon catheterization, endarterectomy, endovascular stent emplacement, or reduction atherectomy, as well as in vascular grafts, organ transplants and catheter emplacements. The present invention provides such methods and fulfills other, related needs.

SUMMARY OF INVENTION

The present invention is directed to methods for inhibiting intimal hyperplasia in the vasculature of a mammal, and to methods of inhibiting platelet-derived growth factor (PDGF) activity.

As used in the present invention;

Alkyl referes to a saturated acyclic hydrocarbon radical.

Alkoxy referes to a saturated acyclic hydrocarbon radical containing at least one oxygen atom.

Mono or Poly-cycloalkyl referes to a radical of a saturated hydrocarbon having one (mono) or more than one (poly) ring.

Bridged mono or polycycloalkyl referes to a mono or polycycloalkyl having one or more bridges which consist of a chemical bond, a single atom, or a chain of atoms, connecting two different parts of the molecule.

Heterocyclic ring referes to a radical of a cyclic compound in which at least one of the ring atoms is not a carbon atom.

The present invention provides methods of inhibiting intimal hyperplasia in the vasculature of a mammal comprising administering an antihyperplastically effective amount of a 4-(2-(N-2-carboxamido indole)aminoethyl) benzenesulfonamide or sulfonylurea of formula I:

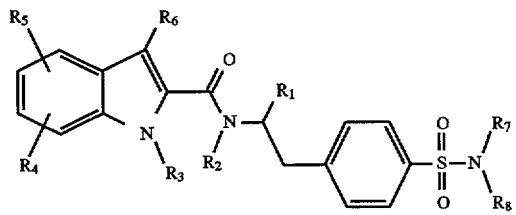

wherein $R_1$, $R_4$, and $R_5$ are individually H, F, Cl, Br, —$CF_3$, or a linear or branched alkyl or alkoxy of from 1 to 6 carbon atoms; $R_2$ and $R_3$ are individually H or a linear or branched alkyl of from 1 to 6 carbon atoms; $R_6$ is H, a linear or branched alkyl or alkoxy of from 1 to 18 carbon atoms, or

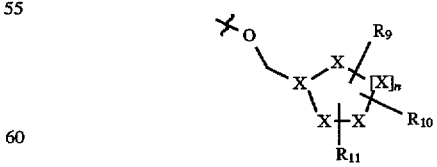

wherein n is 1 or 2; each X is individually C, N, NH, O, and S, with the proviso that at least 1, preferably 2, X are C; $R_9$, $R_{10}$, and $R_{11}$ are individually H, F, Br, Cl, —$CF_3$, or a linear or branched alkyl or alkoxy of from 1 to 6 carbon atoms; $R_7$ and $R_8$ are individually H, a linear or branched alkyl of from 1 to 18 carbon atoms, —CONH—$R_{12}$, or $R_7$ and $R_8$ together with the N that links them form a substituted or unsubstituted heterocyclic ring of from 3 to 8 ring atoms; $R_{12}$ is H,

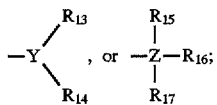

Y is nitrogen; $R_{13}$ and $R_{14}$ are independently H, a linear or branched alkyl of from 1–6 carbon atoms or $R_{13}$ and $R_{14}$ together with the N that links them form a substituted or unsubstituted heterocyclic ring of from 3 to 8 ring atoms; Z is carbon; and $R_{15}$, $R_{16}$ and $R_{17}$ are independently H, a linear or branched alkyl of from 1–6 carbon atoms, $R_{15}$ and $R_{16}$, $R_{16}$ and $R_{17}$, or $R_{15}$ and $R_{17}$ together with Z form a substituted or unsubstituted monocycloalkyl of from 3 to 8 carbon atoms, or $R_{15}$, $R_{16}$, and $R_{17}$ together with Z form a substituted or unsubstituted mono or polycycloalkyl of from 7 to 14 carbon atoms or a substituted or an unsubstituted bridged mono or polycycloalkyl of from 6 to 14 carbon atoms.

Within one embodiment of the invention $R_1$, $R_4$ and $R_5$ are individually H, methyl or methoxy; $R_2$ and $R_3$ are individually H or methyl; $R_6$ is a linear or branched alkoxy of from 1 to 6 carbon atoms, or

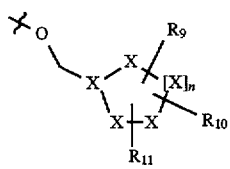

n is 1 or 2; each X is individually selected from the group consisting of C, S and N, with the proviso that 1, preferably 2, X are C; $R_9$, $R_{10}$, and $R_{11}$ are individually H, methyl or methoxy; R7 and Re are individually H, a linear or branched alkyl of 1 to 6 carbon atoms, or CONH—$R_{12}$; $R_{12}$ is H,

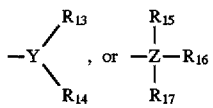

Y is nitrogen; Z is carbon; $R_{13}$ and $R_{14}$ together with Y form a heterocyclic ring of from 5 to 6 ring atoms and $R_{15}$ and $R_{16}$, $R_{16}$ and $R_{17}$, or $R_{15}$ and $R_{17}$ together with Z form a substituted or unsubstituted monocycloalkyl of from 5 to 6 carbon atoms, or $R_{15}$, $R_{16}$, and $R_{17}$ together with Z form a substituted or unsubstituted mono or polycycloalkyl of from 9 to 10 carbon atoms or a substituted or an unsubstituted bridged mono or polycycloalkyl of from 8 to 10 carbon atoms.

Within another related embodiment, $R_7$ and $R_8$ together with the N that links them form an unsubstituted heterocyclic ring of not more than 6 ring atoms.

Within a further embodiment, $R_{13}$ and $R_{14}$ together with Y form the moiety

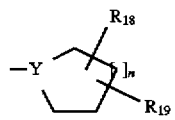

wherein Y is nitrogen, n is 1 or 2, and $R_{18}$ and $R_{19}$ are individually H, F, Br, Cl, —$CF_3$, or a linear or branched alkyl or alkoxy of from 1 to 6 carbon atoms.

Within another embodiment, $R_{15}$ and $R_{16}$, $R_{16}$ and $R_{17}$ or $R_{15}$ and $R_{17}$ together with Z form the moiety

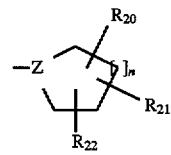

wherein Z is carbon, n is 1 or 2, $R_{20}$, $R_{21}$ and $R_{22}$ are individually H, F, Br, Cl, —$CF_3$, or a linear or branched alkyl or alkoxy of from 1 to 6 carbon atoms.

Within another embodiment, $R_6$ is

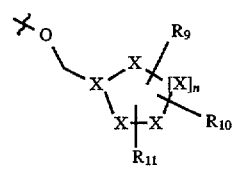

wherein each X is carbon.

Within another embodiment, $R_{18}$ and $R_{19}$ are individually H, methyl, ethyl, methoxy or ethoxy.

A further embodiment provides, $R_{20}$, $R_{21}$, and $R_{22}$ are individually H, methyl, ethyl, methoxy or ethoxy.

Within a preferred embodiment, the invention provides that $R_6$ is benzyloxy.

Within another preferred embodiment, of the invention provides that $R_7$ or $R_8$ is

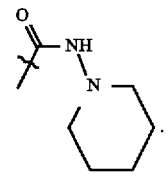

Within a particularly preferred embodiment of the invention, the compound is NNC92-0270:

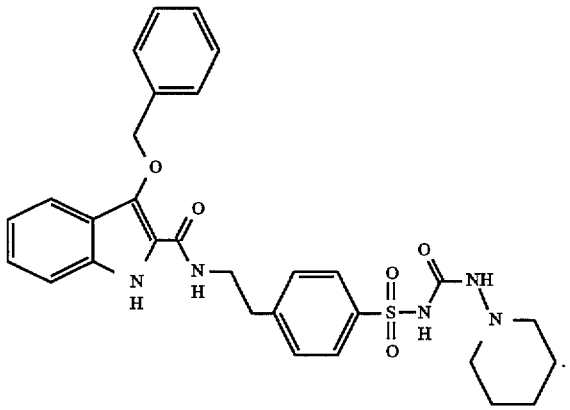

Within a further embodiment of the invention the intimal hyperplasia results from vascular injury, including vascular injury due to vascular reconstruction, such as angioplasty, endarterectomy, reduction atherectomy, endovascular laser ablation or anastomosis of a vascular graft.

Within a further embodiment of the invention, a compound of formula I is administered to a mammal within an antihyperplastically effective time period prior to, concurrent with or subsequent to an acute vascular injury in the mammal.

Within an additional embodiment of the invention, a compound of formula I is administered concurrently with an antihyperplastically effective amount of heparin.

The invention also provides methods of using the compounds of formula I as non-peptide PDGF antagonists, such as for inhibiting PDGF activity in a mammal These and other aspects of the invention will become evident upon reference to the following detailed description of the invention.

DETAILED DESCRIPTION OF THE INVENTION

As noted above, restenosis of blood vessels is a common problem in patients who have undergone angioplasty, endartarectomy, or bypass grafting. Restenosis is one example of intimal hyperplasia, which is believed to proceed via a process that includes both proliferation (mitosis) and migration of vascular smooth muscle cells in the area damaged by the surgical procedure, as well as by the production (deposition) of extracellular matrix. See, in general, Harker, *Am. J. Cardiol.* 60:20B–28B, 1987; and DeFeudis, *Drug News and Perspectives* 5:49–51, 1992. This proliferative process is also manifested in the occlusion of vascular grafts (both natural, including autologous and allogeneic, and synthetic), and in transplanted organs. This proliferative process results in the development of lesions rich in smooth muscle cells and is referred to herein as intimal hyperplasia.

The present invention provides methods for inhibiting the development of SMC-rich lesions (partial or complete blocking of a blood vessel through intimal thickening (hyperplasia)) through the use of a antihyperplastically effective amount of a non-peptide PDGF antagonist, either independently, or in combination with an antihyperplasti-cally effective amount of heparin. Of particular interest for use within the present invention are 4-(2-(N-(2-carboxamidoindole))aminoethyl)benzenesulfonamides of formula I. Non-peptide PDGF antagonists of the current invention may be useful in a therapeutic regime for scleroderma, lung hyperplasia, kidney fibrosis, rheumatoid arthritis, treatment of solid cancers including, but not limited to, osteosarcoma, fibrosarcoma, glioma or other proliferative cellular diseases.

Compounds for use in the present invention can be synthesized using methods well known in the art (see Francia et al., *Boll. Chim. Farm.* 114:379–393, 1975; Vicentini et al., *Il Farmaco. Ed. Sc.* 38:672–678, 1983; Biere et al., *J. of Med. Chem.* 17:716–721, 1973; and Höhn et al., *J. of Med. Chem.* 16:1340–1346, 1973). For example, representative schemes for the syntheses of the compounds of formula I are shown below. The appropriate 2-(Aminoethyl) benzene is first acetylated by reaction with acetic anhydride, and then converted to the benzenesulfonylchloride II by treatment with chlorosulfonic acid. II can then be converted to the desired sulfonamide by treatment with an amine. III directly provides the correct building block for compounds of formula I where $R_7$ and $R_8$ form sulfonamides.

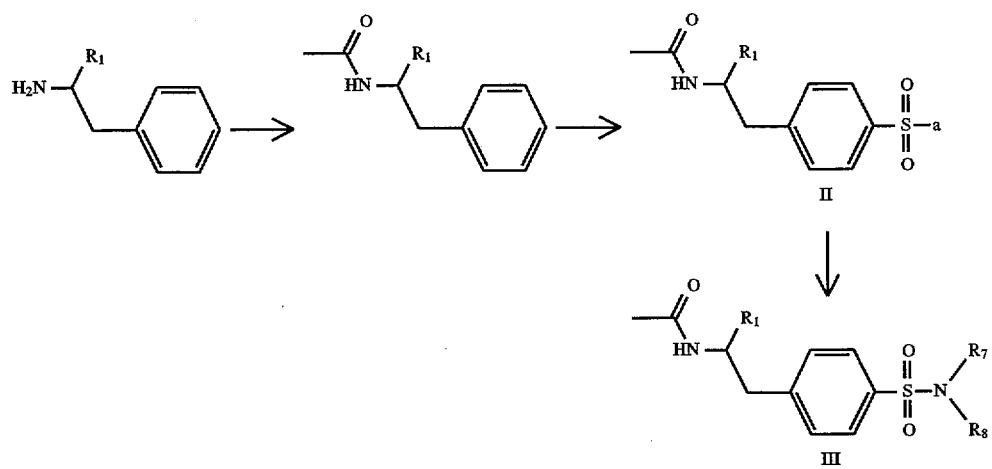

For the synthesis of compounds of formula I where $R_7$ and $R_8$ form sulfonylureas, IV, where $R_7$ and $R_8$ are H, provides the starting material for further manipulations as shown below. IV is first converted to the ethyl sulfonylcarbamate V by treatment with ethylchloroformate. V can then be converted either to VI (or the compound of formula I where $R_7$ or $R_8$ is —$CONH_2$) by reaction with the appropriate amine, or VII by reaction withahydrazine.

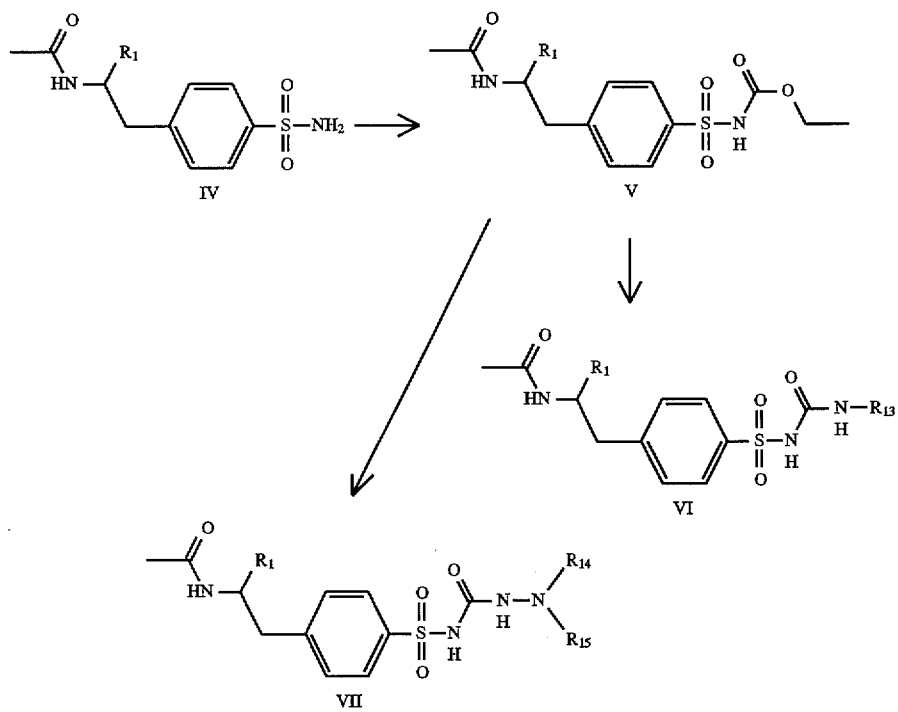

The acetyl amide is hydrolyzed either in aqueous base or acid to give the free amine VIII. VIII can then be acylated with the appropriate indole-2-carboxylic acid chloride to give X, the compounds of formula I. IX is prepared by the reaction of the corresponding indole-2-carboxylic acid with oxalyl chloride. The indole-2-carboxylic acids are prepared by one of the many methods known to those skilled in the art.

The preparation of compounds representative of more unusual 3-alkoxyindoles (where $R_6$ is alkoxy or the methoxy-ring compounds described) is shown below. The Ethyl 2-aminobenzoate is N-alkylated with ethyl α-bromoacetate to give XI. Treatment of XI with sodium ethoxide affords the 3-oxoindole XII. Alkylation with the appropriate alkyl halide gives the 3-alkoxyindole XIII.

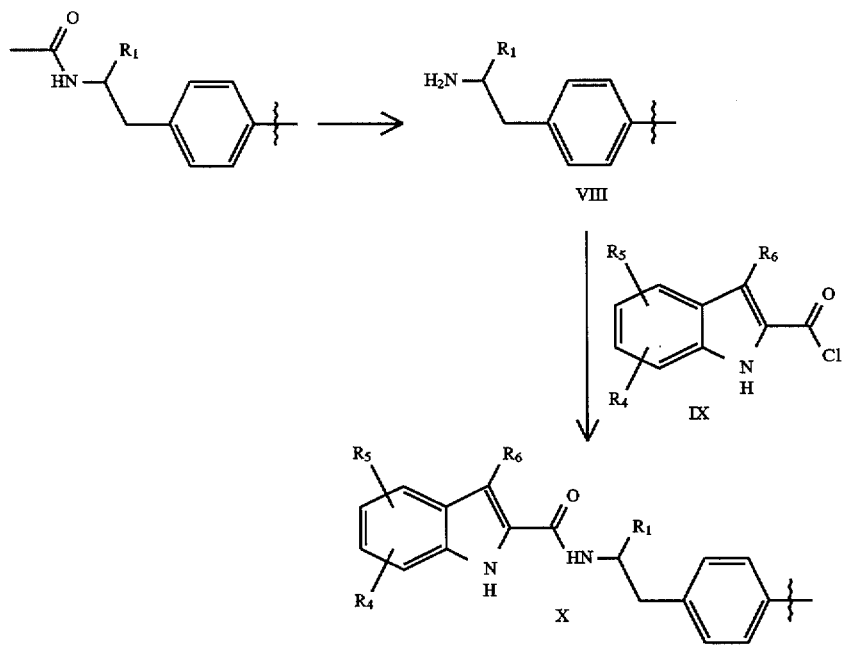

Saponification, followed by reaction with oxalyl chloride gives the acid chloride XV.

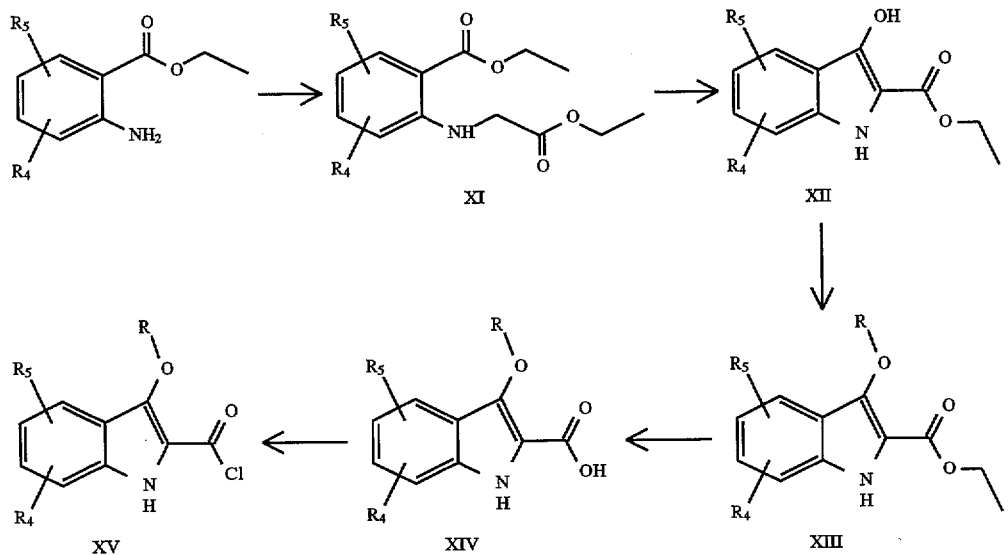

As used herein, the term "non-peptide PDGF antagonist" refers to a compound, other than a peptidic compound, that inhibits a PDGF-induced stimulation of a response pathway. A "response pathway" is a biochemical pathway activated in response to external stimuli that is generally, but no always, directly coupled to a membrane-bound receptor. Response pathways generally induce cellular responses such as, extracellular matrix secretion from responsive cell lines, hormone secretion, chemotaxis, differentiation or the stimulation of cell division of responsive cells.

PDGF receptors are integral, transmembrane glycoproteins whose expression is generally limited to cells of mesodermal origin. Two PDGF receptor polypeptides have been described. These are termed "alpha receptor" (Kelly et al., WO 90/14425; Kelly et al., U.S. Pat. No. 5,371,205; Claesson-Welsh et al., Proc. Natl. Acad. Sci. USA 86: 4917–4921, 1989) and "beta receptor" (Claesson-Welsh et al., Mol. Cell. Biol. 8: 3476–3486, 1988; Gronwald et al., Proc. Natl. Acad. Sci. USA 85: 3435–3439, 1988). In the presence of PDGF ligand, the receptor polypeptides dimerize. Three receptor subtypes are thus possible: αα, αβ and ββ. The β receptor is specific for the B-chain of PDGF, while the α receptor binds the A-chain and the B-chain. Consequently, the growth regulatory responsiveness of cells to PDGF depends not only on the availability of PDGF AA, AB and BB ligand isoforms, but also on the expression and availability of different PDGF receptor subtypes (Heldin et al., Cell Regul. 1: 555–566, 1990). Human smooth muscle cells express both alpha and beta receptor subtypes (Heldin et al., Cell Regul, 1: 555–566, 1990), but other cell types are known which express only a single receptor subtype (Gronwald et al., J. Biol. Chem. 264: 8120–8125, 1989). The present invention also provides methods for inhibition of intimal hyperplasia by coordinately administering an antihyperplastically effective amount of a non-peptide PDGF antagonist and an antihyperplastically effective amount of heparin. As used herein, the term "heparin" refers to any member of a family of structurally complex, sulphated glycosaminoglycans generally characterized by a structure of repeating glucosamine and glucuronic acid sugar residues (Casu, Adv. Carbohyd. Chem. and Biochem, 47: 578–583, 1985). The most widely known heparin is "unfractionated" or "commercial" heparin prepared from bovine lung or porcine gut, which encompasses a heterogeneous mixture of heparin molecules ranging from approximately 8,000 to 20,000 daltons molecular weight (Wolinsky et al., J. Am. Coll. Cardiol. 15: 475–481, 1990). However, the term heparin also encompasses a broad range of more homogeneous heparin preparations, as well as heparin-like molecules, including heparan sulfates. Among these particular heparin examples, more specific heparin subtypes are also known. For example, heparan sulfate moieties produced by endothelial cells (Castellot et al., J. Cell. Biol. 90: 372–379, 1981) and smooth muscle cells (Fritze et al., J. Cell. Biol, 1041–1049, 1985) have been isolated which are reportedly up to 40 times more active than unfractionated heparin for inhibiting proliferation of smooth muscle cells. In addition, among the naturally occurring heparin size variants, fractionated heparin species that exhibit predominantly either anticoagulant or antiproliferative activity have been isolated (Wolinsky et al., J. Am. Coll. Cardiol. 15: 475–481, 1990). The latter activity tends to be present in the low molecular weight heparin species, such as heparins in the range of penta- to decasaccharides, which have been reported to also provide greater bioavailability and a longer half-life (Id., Bacher et al., Thrombosis Res. 70: 295–306, 1993), and may therefore be particularly useful within specific embodiments of the invention. Also included within the definition of heparin for the purposes of describing the invention are synthetic heparins and heparin derivatives, a variety of which have been produced using conventional chemical synthetic, modifying and degradative techniques (see for example, Roden, L. The Biochemistry of Glycoproteins and Proteoglycans (Lennarz, W. J., ed.) pp 267–371, Plenum Publishing Corp., New York, 1980, incorporated herein by reference).

An "antihyperplastically effective amount" of a compound is defined as an amount of a compound sufficient to measurably reduce or prevent intimal hyperplasia in a blood vessel, vessel graft or vascular component of a transplanted organ. More specifically, "inhibition of intimal hyperplasia" is herein defined to include any measurable inhibition of one or more of the intimal hyperplastic processes described in the art, such as vascular smooth muscle cell (VSMC)

migration, VSMC proliferation, and neointimal deposition of extracellular matrix. In this context, reduction or prevention of intimal hyperplasia, or of a hyperplastic process involved in intimal hyperplasia, can be readily evaluated using in vitro, in vivo and ex vivo assay systems known in the art, in particular primate-based assay systems (e.g., non-human or human primate VSMC cultures or vascular tissue explants, or non-human primate in vivo tests). By preventing PDGF from exerting its stimulatory effect, SMC proliferation and subsequent matrix deposition may be reduced. A reduction in intimal hyperplasia is clinically manifested as a significant decrease in loss of lumenal volume after an acute vascular injury. Such a reduction will generally result in a decreased need for re-vascularization procedures (e.g., repeat angioplasty) at the site of the initial injury. The methods of the present invention are particularly useful in the treatment of intimal hyperplasia due to acute vascular injury. Acute vascular injuries are those which occur rapidly (i.e. over days to months), in contrast to chronic vascular injuries (e.g. atherosclerosis) which develop over a lifetime. Acute vascular injuries often result from surgical procedures such as vascular reconstruction, wherein the techniques of angioplasty, endarterectomy, reduction atherectomy, endovascular stenting, endovascular laser ablation, anastomosis of a vascular graft or the like are employed. Hyperplasia may also occur as a delayed response in response to, e.g., emplacement of a vascular graft or organ transplantation.

In humans treated with non-peptide PDGF antagonist therapy, either alone, or in combination with heparin, the antagonist may be given under a wide range of conditions. The antagonist can be given via bolus injections, both prior to the re-vascularization procedure as well a multiple times following the procedure. The antagonist may be given orally, as a bolus injection (intravenous, intramuscular, intraperitoneal or subsutaneous) prior to the procedure (generally within 24 hours before surgery) and a constant infusion following the procedure (including infusion via implanted pumps). In many cases it will be preferable to administer daily doses (including administration by infusion) during a hospital stay, followed by less frequent bolus injections during a period of outpatient treatment of one to two weeks or more. Treatment may be continued for up to six months after initial injury. The antagonist may be given via multiple routes including intravenous, intramuscular or subcutaneous injections. In addition the antagonist may be delivered locally to the site of vascular injury using perfusion balloon catheters, coating onto stents, or placement on gel coated balloons. In the latter cases it would be expected that the doses of antagonist would be substantially less than that required when given systemically. The antagonist may also be delivered by slow-release delivery systems, including such systems incorporated into vascular grafts or stents, or by way of perfusion of double balloon catheters. Pumps or other known delivery systems may also be employed.

In an alternate embodiment of the invention, a non-peptide PDGF antagonist is administered to a mammal coordinately with heparin, in respective unit doses of antagonist and heparin sufficient to combinatorially inhibit intimal hyperplasia in the vasculature of the mammal. In this context, "coordinate administration" is intended to include concurrent, separate or sequential administration of the antagonist and heparin, wherein both the antagonist and heparin are administered within a limited, combinatorially effective time period relative to one another. A "combinatorially effective time period" is defined as a maximum intervening time period between administration of the antagonist and administration of the heparin in which the two agents are combinatorially effective in inhibiting the hyperplasia. The term "combinatorially effective" is in turn defined as producing a measurable inhibition of intimal thickening or lesion formation, or of a hyperplastic process, which exceeds a maximum level of inhibition independently provided by either the antibody or heparin administered alone, under otherwise comparable conditions and dose.

Generally, doses of heparin will be between approximately 1ug-100 mg/kg/day. Preferably, heparin doses will be between 29 µg-10 mg/kg/day, and more preferably less than about 1 mg/kg/day. Those skilled in the art will recognize that actual doses will be determined with consideration of specific circumstances, including patient parameters and the characteristics of the antagonists and heparin administered.

The inhibition of hyperplasia will be expected to lead to a decrease in clinical events in patients. These events include a decrease in one or more myocardial infarcts, angina, the need for revascularization procedures, and death.

The following examples are offered by way of illustration, not by way of limitation.

EXAMPLES

Example 1

Antagonist Assay

Initial characterization of NNC92-0270 as a non-peptide PDGF antagonist was made possible through an SRE-Luciferase high through-put assay system which involves selection of substances that are able to block expression of a serum response element (SRE)-luciferase reporter gene expressed in SWISS3T3 cells. The SRE-luciferase construct, pKZ67, is a pUC18-derived mammalian cell expression vector comprising a luciferase expression unit that includes a synthesized segment containing human c-fos sequence from −360 to +30 (van Straaten et al., *Proc. Natl. Acad. Sci. USA* 80:3183–3187, 1983) (including TATA, SRE and SIE promoter elements), a luciferase sequence (Delegeane et al., *Mol. Cell Biol.* 7:3994–4002, 1987; deWet et al., *Mol. Cell. Biol.* 7:725–737, 1987), and a human growth hormone gene terminator. This expression unit is in opposite transcriptional orientation to a second expression unit that includes a neomycin resistance marker flanked by SV40 promoter and terminator sequences. SWISS3T3 cells express endogenous growth factor receptors such as, PDGF-AA, -AB and -BB; bFGF and EGF. Stimulating the receptors with any of these growth factors initiates a signal cascade leading to induction of luciferase. PMA (phorbol 12-myristate 13-acetate) bypasses the receptor and initiates an internal signal cascade by stimulating protein kinase C, which leads to the induction of luciferase. The degree of antagonist specificity can be determined by comparing the resultant signal for the three growth factors (PDGF, bFGF and EGF). Compounds resulting in a 50 fold signal reduction compared to the control were considered for further analysis.

SWISS3T3 cells (transfected with a SRE-luciferase reporter gene, SWISS3T3/KZ67-G1-6) were maintained by serial passage in maintenance medium (DMEM (GIBCO BRL, Gaithersburg, Md.) supplemented with 10% fetal bovine serum (FBS), 2 mM L-glutamine, 1 mM sodium pyruvate, 1 mg/ml G418). Two days prior to assay, cells were trypsinized, adjusted to $5 \times 10^4$ cells/well in growth medium (DMEM supplemented with 1% FBS, 2 mM L-glutamine, 1 mM sodium pyruvate), plated in opaque white 96-well microtiter plates at 200 µl/well (1×10⁴ cells/well) and grown for 48 hours at 37° C., 5% $CO_2$.

Test substances were prepared in 4% DMSO. Induction was initiated by removing spent medium from the wells and adding 50 µl/well assay medium (F12 HAM (Gibco) supplemented with 0.5% Fraction V BSA (Sigma, St. Louis, Mo.), 2 mM L-glutamine, 1 mM sodium pyruvate, 20 mM Hepes. Twenty five microliters of either 50 ng/ml PDGF (final assay concentration 12.5 ng/ml) or 8 ng/ml bFGF (final assay concentration 2.0 ng/ml) in assay medium were added to the wells. Controls, prepared in assay medium, were included on each plate: untreated wells (basal), 12.5 ng/ml, more preferably 6.25 ng/ml, PDGF BB (platelet derived growth factor, stock 10 µg/ml 10 mM Acetic acid, 0.25% RSA in PBS), 2.0 ng/ml bFGF (basic fibroblast growth factor (Genzyme Diagonstics, Cambridge, Mass.)), 4.5 ng/ml EGF (epidermal growth factor (Sigma)) or 50 ng/ml PMA (Sigma). Final assay concentration of DMSO do not exceed 1%. Plates were incubated for 5 hours at 37° C., 5% $CO_2$.

Following induction, luciferase activity was measured using a Promega luciferase assay kit (E1500; Promega Corp., Madison, Wis.) according to the assay kit protocol. Briefly, assay medium was removed from the plate, and 25 µl/well cell lysis buffer, diluted 1:5 with sterile water, was added to the plate. Plates were incubated for 15 minutes. The plates were transferred to a Lumiskan™ (ICN Biomedical, Cleveland, Ohio) microtiter luminometer, which added 40 µl/well Luciferase Assay substrate (Promega Corp.). The amount of luminescence (relative light units, RLU) was determined following a 1 second mix and a 1–3 integration of signal. Basal (uninduced) luciferase signal was subtracted from all measurements, and the luciferase signal induced by test samples was expressed as a percentage of the signal in the control. Data presented in Table 1 show the approximate effective dose of NNC92-0270 to inhibit 50% of the control activity ($IC_{50}$).

TABLE 1

| Induction of SRE-luciferase | | | |
|---|---|---|---|
| PDGF $IC_{50}$ (µM) | bFGF $IC_{50}$ (µM) | EGF $IC_{50}$ (µM) | PMA $IC_{50}$ (µM) |
| 13 | >100 | No activity | >100 |

Example 2

Inhibition of ¹²⁵I-PDGF-BB Binding to Rat Smooth Muscle Cells (SMCs)

NNC92-0270 was analyzed for the ability to inhibit ¹²⁵I-PDGF-BB binding to monolayers of rat SMCs. To assay for inhibition of ¹²⁵I-PDGF-BB binding to rat SMCs, the SMCs were plated at approximately 20,000 cells/well in 24-well culture dishes. The cells were used for assay 2–7 days after plating. The test compound was diluted in binding media (500 ml Ham's F-12 (Gibco BRL), 12 ml 1M Hepes pH 7.4, 5 ml 100×PSN (Gibco BRL), 1 gm rabbit serum albumin (Sigma Chemical Co., St. Louis, Mo.) to the concentrations shown in Table 2, then added to the SMCs (1 ml/well) in triplicate. To the wells was then added 50 µl of a ¹²⁵I-PDGF-BB stock solution. Binding media alone was used as the negative control, and the addition of 200 ng/ml of PDGF-BB was used to determine nonspecific binding for ¹²⁵I-PDGF-BB. The cells were incubated for approximately 1½ hours at 4° C., then washed with binding media to remove unbound ligand. The cells were then incubated with extraction buffer (20 mM Tris-HCl, pH 8.0, 100 mM NaCl, 1 mM EDTA, 0.5% Nonident P-40, 0.5% sodium deoxycholate, 10 mM NaI, 1% bovine serum albumin), and the extracts were harvested and counted in a gamma counter. The results of the binding studies are shown in Table 2. The data are presented as specific cpm bound for ¹²⁵I-PDGF-BB. Nonspecific binding, determined by the addition of 200 ng/ml of unlabeled PDGF-BB, was 853 cpm, and has been subtracted from the data presented.

TABLE 2

| Inhibition of ¹²⁵I-PDGF-BB Binding to Rat SMCs | | | |
|---|---|---|---|
| Compound | Concentration (µM) | ¹²⁵I PDGF-BB Bound (CPM) | % Control Binding |
| NNC92-0270 | 100 | 378 | 4 |
|  | 50 | 532 | 5 |
|  | 25 | 920 | 9 |
|  | 12.5 | 2823 | 28 |
|  | 6.2 | 5228 | 52 |
| Negative Control |  | 10006 | 100 |

These results demonstrate NNC92-0270 is a potent inhibitor of PDGF-BB binding to cell-surface PDGF receptors.

NNC92-0270 was subsequently analyzed for its ability to inhibit ¹²⁵I-PDGF-BB binding to rat SMCs when the radioligand was added to the cells in the presence of 10% human serum. The rat SMCs were plated into 24-well culture dishes and assayed as described above. The test compound was diluted to the concentrations shown in Table 3 in either binding media alone, or binding media containing 10% human serum, and 1 ml aliquots added to the test cells in triplicate. Fifty microliters of a 20×stock solution of ¹²⁵I-PDGF-BB was added to each well. The cells were incubated for 2.5 hours at 4° C., washed with binding media to remove unbound ligand, and harvested with extraction buffer. The extracts were then counted in a gamma counter to determine CPM bound. The results, presented in Table 3, demonstrate that NNC92-0270 has approximately equal potency for inhibiting ¹²⁵I-PDGF-BB binding when diluted in the binding media containing 10% human serum as compared to that diluted in binding media alone. It should be noted that the binding of ¹²⁵I-PDGF-BB was lower in the negative control sample containing the human serum, over the negative control sample with binding media alone. The results are presented as total CPM bound.

TABLE 3

| Inhibition of ¹²⁵I-PDGF-BB Binding to Rat SMCs in the Presence and Absence of Human Serum. | | | | | |
|---|---|---|---|---|---|
|  |  | Binding Media | | Binding Media + 10% Human Serum | |
| Compound | Conc. (µM) | CPM Bound | % CB | CPM Bound | % CB |
| NNC92-0270 | 50 | 467 | 23 | 162 | 14 |
|  | 25 | 605 | 30 | 244 | 21 |
|  | 12.5 | 722 | 36 | 349 | 30 |
| Neg. Cont. |  | 1990 |  | 1152 |  |

% CB = % Control Binding

Example 3

Inhibition of PDGF-BB Mitogenic Activity on Baboon Smooth Muscle Cells

NNC92-0270 was analyzed for the ability to inhibit the mitogenic activity of PDGF on baboon smooth muscle cells.

All mitogenesis assays performed on baboon vascular smooth muscle cells (BVSMCs) were done on primary cultures of cells between passages 13 and 20 in culture. The initial cultures were established from outgrowth of aortic tissue explants. Baboon smooth muscle cells were plated at approximately 20,000 cells per well, in DMEM supplemented with 10% fetal calf serum, into 24-well culture dishes. One day prior to use the culture media was removed, and 1 ml of Mito Media (Table 5) was added to each well to allow the cells to become quiescent. At the time of the experiment the cells were stimulated with PDGF-BB. A standard curve was run for PDGF-BB with concentrations of 1, 0.5, 0.25, 0.062, and 0 ng/ml. 20× stock solutions were made for each of the PDGF concentrations by dilution in 10 mM acetic acid containing 0.25% albumin, and 50 ul PDGF or dilution vehicle alone was added to the culture wells.

To analyze the activity of NNC92-0270 to neutralize PDGF-BB mitogenic activity, 1 ng/ml of PDGF was added to wells along with dilutions of NNC92-0270. The cells were incubated with the test samples for approximately 20 hours at 37 ° C. Fifty microliters of a 20× stock solution of [3H] Thymidine was then added to each well to give a final concentration of 1 µCi/ml. The cells were incubated for 4 hours at 37 ° C., washed with PBS, then harvested with trypsin and counted for [$^3$H] thymidine incorporation in a Wallac (Turku, Finland) Betaplate™ liquid scintillation counter. The results, presented in Table 4, demonstrate that PDGF-BB mitogenic activity was inhibited by NNC92-0270 in a dose dependent fashion. The $ED_{50}$ for the inhibition was approximately 12.5 µM for NNC92-0270.

TABLE 4

Inhibition of PDGF-BB Mitogenic Activity on Baboon Smooth Muscle Cells

| Compound | Conc. | $^3$H Thymidine (CPM Incorporated) | |
| --- | --- | --- | --- |
| | | (−) Heparin | (+) 0.5 U/ml Heparin |
| PDGF-BB | 1 ng/ml | 1701 | |
| | 0.5 | 959 | |
| | 0.25 | 392 | |
| | 0.125 | 226 | |
| | 0.062 | 120 | |
| | 0 | 74 | |
| PDGF-BB/NNC92-0270 (1 ng/ml) | 50 µM | 309 | 211 |
| | 25 | 334 | 220 |
| | 12.5 | 870 | 586 |
| | 6.2 | 1378 | 1007 |
| | 0 | 1701 | 1089 |

As part of this same experiment, the inhibitory potency of NNC92-0270 was analyzed in the presence of heparin. We have previously demonstrated that heparin is able to act in a combinatorial manner with neutralizing monoclonal antibodies to the PDGF receptor to inhibit PDGF mitogenic activity on baboon smooth muscle cells. We wished to determine if the presence of heparin would have a similar potentiating effect with NNC92-0270 for inhibiting PDGF-BB mitogenic activity.

NNC92-0270 was incubated with 1 ng/ml of PDGF-BB in the presence of 0.5 U/ml of unfractionated heparin. The cells were pulse labeled with [$^3$H] thymidine as described above and the level of [$^3$H] thymidine determined. The results are presented in Table 4.

These results demonstrate that the addition of heparin to NNC92-0270 led to a further inhibition of [$^3$H] thymidine above that achieved by NNC92-0270 alone.

Example 5

Wash Out Study

NNC92-0270 was analyzed for prolonged inhibitory effect on PDGF-BB mitogenic activity on baboon smooth muscle cells in a wash-out experiment. Baboon SMCs were plated at 20,000 cells per well in a 24-well culture dish and grown for 2 days. The culture media was removed and replaced with Mito Media (Table 5) to allow the cells to become quiescent. The experiment was set up such that cells were treated with NNC92-0270 or vehicle control (0.5% DMSO) for either 24 hours prior to the addition of PDGF-BB, or sequentially with the addition of PDGF-BB. Those cells initially treated with NNC92-0270 or control vehicle for 24 hours, were washed with Mito Media to remove the test compound and then incubated with PDGF-BB (1 ng/ml) for an additional 24 hours. A second set of cells was treated with NNC92-0270 or vehicle control simultaneously with PDGF-BB for 24 hours. The cells were pulse labeled for 4 hours with [$^3$H] thymidine (1 µCi/ml final) harvested with trypsin and counted in a Wallac Betaplate counter to determine CPM for [$^3$H] thymidine incorporation.

The results, presented in Table 6, are given as the mean ± standard deviation for [$^3$H] thymidine incorporation for triplicate determinations. Acetic acid (10 mM) was used as the PDGF-BB vehicle control and 0.5% DMSO was used as the test compound control.

Table 5

Mito Media

For a 500 ml solution:

250 ml DMEM (GIBCO BRL)

250 ml Ham's F-12 (GIBCO BRL)

0.25 ml 10 mg/ml stock of insulin (GIBCO BRL) to give a final concentration of 5 µg/ml 1 ml 10 mg/ml stock of transferrin (Collaborative Research, Bedford, Mass.) to give a final concentration of 20 µg/ml 2 ml 4 µg/ml stock of selenium (Aldrich Chemical, Milwaukee, Wis.) to give a final concentration of 5 nM 5 ml 10% stock solution of bovine serum albumin (GIBCO BRL) to give a final concentration of 0.1%.

TABLE 6

Wash-Out Experiment to Study the Prolonged Effect of NNC92-0270 on PDGF-BB Mitogenic Activity on Baboon Smooth Muscle Cells.

| Test Conditions | | [3H] Thymidine Incorporation (cpm) |
| --- | --- | --- |
| 1. | T = −24 hrs (0.5% DMSO) T = 0 hrs (PDGF-BB) | 6370 +/− 1303 |
| 2. | T = −24 hrs. (0.5% DMSO) T = 0 hrs (PDGF-BB/NNC92-02700) | 678 +/− 68 |
| 3. | T = −24 hrs (92-02700) T = 0 hrs. (PDGF-BB) | 5735 +/− 474 |
| 4. | T = −24 hrs. (0.5% DMSO) T = 0 hrs. (Acetic Acid) | 164 +/− 10 |
| 5. | T = −24 hrs. (NNC92-02700) T = 0 hrs. (Acetic Acid) | 237 +/− 36 |

From the foregoing, it will be appreciated that, although specific embodiments of the invention have been described herein for purposes of illustration, various modifications may be made without deviating from the spirit and scope of the invention. Accordingly, the invention is not limited except is by the appended claims.

We claim:

1. A method of inhibiting intimal hyperplasia in the vasculature of a mammal comprising administering to said mammal an antihyperplastically effective amount of a platelet derived growth factor (PDGF) antagonist of Formula I:

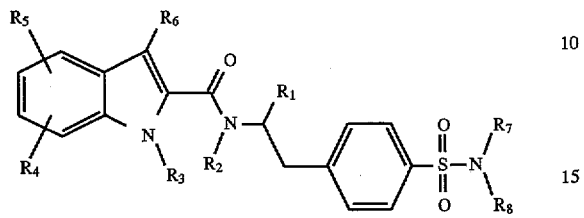

wherein $R_1$, $R_4$, and $R_5$ are individually H, F, Cl, Br, —$CF_3$, or a linear or branched alkyl or alkoxy of from 1 to 6 carbon atoms;

$R_2$ and $R_3$ are individually H or a linear or branched alkyl of from 1 to 6 carbon atoms;

$R_6$ is H, a linear or branched alkyl or alkoxy of from 1 to 18 carbon atoms, or

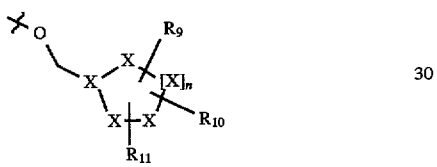

n is 1 or 2;

each X is individually C, N, NH, O, and S, with the proviso that at least 1–2 X are C;

$R_9$, $R_{10}$, and $R_{11}$ are individually H, F, Br, Cl, —$CF_3$ or a linear or branched alkyl or alkoxy of from 1 to 6 carbon atoms;

$R_7$ and $R_8$ are individually H, a linear or branched alkyl of 1 to 18 carbon atoms, —CONH—$R_{12}$, or $R_7$ and $R_8$ together with the N that links them form a heterocyclic ring of from 3 to 8 ring atoms;

$R_{12}$ is H,

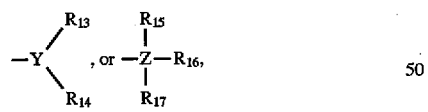

Y is nitrogen;

$R_{13}$ and $R_{14}$ are independently H, a linear or branched alkyl of from 1–6 carbon atoms or $R_{13}$ and $R_{14}$ together with the N that links them form a heterocyclic ring of from 3 to 8 ring atoms;

Z is carbon; and $R_{15}$, $R_{16}$ and $R_{17}$ are independently H, a linear or branched alkyl of from 1–6 carbon atoms, $R_{15}$ and $R_{16}$, $R_{16}$ and $R_{17}$, or $R_{15}$ and $R_{17}$ together with Z form a monocycloalkyl of from 3 to 8 carbon atoms, or $R_{15}$, $R_{16}$, and $R_{17}$ together with Z form a mono or polycycloalkyl of from 7 to 14 carbon atoms or a bridged mono or polycycloalkyl of from 6 to 14 carbon atoms.

2. A method according to claim 1 wherein $R_1$, $R_4$ and $R_5$ are individually H, methyl or methoxy;

$R_2$ and $R_3$ are individually H or methyl;

$R_6$ is a linear or branched alkoxy of from 1 to 6 carbon atoms, or

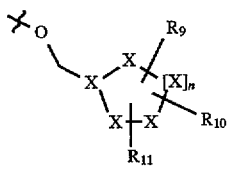

n is 1 or 2;

each X is individually selected from the group consisting of C, S and N, with the proviso that 1–2 X are C;

$R_9$, $R_{10}$, and $R_{11}$ are individually H, methyl or methoxy;

$R_7$ and $R_8$ are individually H, a linear or branched alkyl of 1 to 6 carbon atoms, or CONH—$R_{12}$;

$R_{12}$ is H,

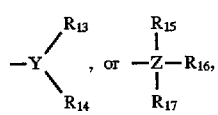

Y is nitrogen;

Z is carbon;

$R_{13}$ and $R_{14}$ together with Y form a heterocyclic ring of from 5 to 6 ring atoms and $R_{15}$ and $R_{16}$, $R_{16}$ and $R_{17}$, or $R_{15}$ and $R_{17}$ together with Z form a monocycloalkyl of from 5 to 6 carbon atoms, or $R_{15}$, $R_{16}$, and $R_{17}$ together with Z form a mono or polycycloalkyl of from 9 to 10 carbon atoms or a bridged mono or polycycloalkyl of from 8 to 10 carbon atoms.

3. A method according to claim 1 wherein $R_7$ and $R_8$ together with the N that links them form an unsubstituted heterocyclic ring of not more than 6 ring atoms.

4. A method according to claim 1 wherein $R_{13}$ and $R_{14}$ together with Y form the moiety

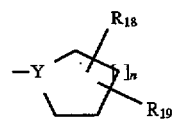

wherein

Y is nitrogen, n is 1 or 2, and $R_{18}$ and $R_{19}$ are individually H, F, Br, Cl, —$CF_3$, or a linear or branched alkyl or alkoxy of from 1 to 6 carbon atoms.

5. A method according to claim 1 wherein $R_{15}$ and $R_{16}$, $R_{16}$ and $R_{17}$ or $R_{15}$ and $R_{17}$ together with Z form the moiety

19

[structure: -Z—[ring with R20, R21, R22]n]

wherein

Z is carbon, n is 1 or 2, and $R_{20}$, $R_{21}$ and $R_{22}$ are individually H, F, Br, Cl, —$CF_3$, or a linear or branched alkyl or alkoxy of from 1 to 6 carbon atoms.

6. A method according to claim 1 wherein $R_6$ is

[structure with R9, R10, R11, X groups, n]

wherein each X is carbon.

7. A method according to claim 4 wherein $R_{18}$ and $R_{19}$ are individually H, methyl, ethyl, methoxy or ethoxy.

8. A method according to claim 5 wherein $R_{20}$, $R_{21}$, and $R_{22}$ are individually H, methyl, ethyl, methoxy or ethoxy.

9. A method according to claim 1 wherein $R_6$ benzyloxy.

10. A method according to claim 1 wherein $R_7$ or $R_8$ is

[structure: C(=O)—NH—N(piperidine)]

11. A method according to claim 1 wherein said non-peptide PDGF antagonist is NNC92-0270:

[chemical structure]

12. A method according to claim 1 wherein said mammal is a primate.

13. A method according to claim 1 wherein said non-peptide PDGF antagonist is administered concurrently with, or within an antihyperplastically effective time period before, an acute vascular injury in said mammal.

14. A method according to claim 13 wherein said injury is due to vascular reconstruction.

20

15. A method according to claim 14 wherein said vascular reconstruction comprises angioplasty, endarterectomy, reduction atherectomy, endovascular laser ablation, or anastomosis of a vascular graft.

16. A method according to claim 1 wherein said non-peptide PDGF antagonist is administered within an antihyperplastically effective time period following an acute vascular injury in said mammal.

17. A method according to claim 16 wherein said injury is due to vascular reconstruction.

18. A method according to claim 17 wherein said vascular reconstruction comprises angioplasty, endarterectomy, reduction atherectomy, endovascular laser ablation, or anastomosis of a vascular graft.

19. A method of claim 1 for inhibiting intimal hyperplasia in the vasculature of a mammal, comprising:

coordinately administering to said mammal an antihyperplastically effective amount of a non-peptide PDGF antagonist and an antihyperplastically effective amount of heparin, wherein said coordinately administered non-peptide PDGF antagonist and heparin are combinatorially effective to inhibit said hyperplasia.

20. A method according to claim 19, wherein said non-peptide PDGF antagonist and heparin are administered to said mammal by a mode of administration selected from the group consisting of oral, intravascular, perivascular, transdermal and rectal administration modes.

21. A method of inhibiting PDGF activity in a mammal comprising administering to said mammal an amount of a compound of formula I:

[chemical structure of formula I with R1–R8 substituents]

wherein $R_1$, $R_4$, and $R_5$ are individually H, F, Cl, Br, —$CF_3$, or a linear or branched alkyl or alkoxy of from 1 to 6 carbon atoms;

$R_2$ and $R_3$ are individually H or a linear or branched alkyl of from 1 to 6 carbon atoms;

$R_6$ is H, a linear or branched alkyl or alkoxy of from 1 to 18 carbon atoms, or

[structure with R9, R10, R11, X groups, n]

n is 1 or 2;

each X is individually C, N, NH, O, and S, with the proviso that at least 1–2 X are C;

$R_9$, $R_{10}$, and $R_{11}$ are individually H, F, Br, Cl, —$CF_3$ or a linear or branched alkyl or alkoxy of from 1 to 6 carbon atoms;

$R_7$ and $R_8$ are individually H, a linear or branched alkyl of from 1 to 18 carbon atoms, —CONH—$R_{12}$, or $R_7$ and $R_8$ together with the N that links them form a heterocyclic ring of from 3 to 8 ring atoms;

$R_{12}$ is H,

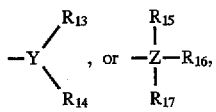

Y is nitrogen;

$R_{13}$ and $R_{14}$ are independently H, a linear or branched alkyl of from 1–6 carbon atoms or $R_{13}$ and $R_{14}$ together with the N that links them form a heterocyclic ring of from 3 to 8 ring atoms;

Z is carbon; and $R_{15}$, $R_{16}$ and $R_{17}$ are independently H, a linear or branched alkyl of from 1–6 carbon atoms, $R_{15}$ and $R_{16}$, $R_{16}$ and $R_{17}$, or $R_{15}$ and $R_{17}$ together with Z form a monocycloalkyl of from 3 to 8 carbon atoms, or $R_{15}$, $R_{16}$, and $R_{17}$ together with Z form a mono or polycycloalkyl of from 7 to 14 carbon atoms or a bridged mono or polycycloalkyl of from 6 to 14 carbon atoms.

\* \* \* \* \*